US010858611B2

(12) United States Patent
Verraes et al.

(10) Patent No.: US 10,858,611 B2
(45) Date of Patent: Dec. 8, 2020

(54) PROCESS FOR PREPARING MIXTURES OF EPOXIDIZED FATTY ACID ESTERS

(71) Applicant: PROVIRON HOLDING N.V., Hemiksem (BE)

(72) Inventors: Arnaud Verraes, Hemiksem (BE); Jelle Cornelus, Hemiksem (BE)

(73) Assignee: Proviron Holding N.V., Hemiksem (BE)

( * ) Notice: Subject to any disclaimer, the term of this patent is extended or adjusted under 35 U.S.C. 154(b) by 0 days.

(21) Appl. No.: 16/646,011

(22) PCT Filed: Sep. 26, 2018

(86) PCT No.: PCT/EP2018/025251
§ 371 (c)(1),
(2) Date: Mar. 10, 2020

(87) PCT Pub. No.: WO2019/063130
PCT Pub. Date: Apr. 4, 2019

(65) Prior Publication Data
US 2020/0208078 A1  Jul. 2, 2020

(30) Foreign Application Priority Data
Sep. 27, 2017 (BE) .................................. 2017/0138

(51) Int. Cl.
*C07D 303/42* (2006.01)
*C11C 3/00* (2006.01)
*C11C 1/10* (2006.01)

(52) U.S. Cl.
CPC ............... *C11C 3/006* (2013.01); *C11C 1/10* (2013.01); *C11C 3/003* (2013.01)

(58) Field of Classification Search
CPC . C11C 3/006; C11C 3/003; C11C 1/10; C11B 3/12; C08G 59/027; C07D 303/42
(Continued)

(56) References Cited

U.S. PATENT DOCUMENTS

| 2002/0013396 A1 | 1/2002 | Benecke et al. |
| 2012/0289727 A1 | 11/2012 | Cordeiro et al. |
| 2016/0060426 A1 | 3/2016 | Woldt et al. |

FOREIGN PATENT DOCUMENTS

| WO | WO 2013/003225 A2 | 1/2013 |
| WO | WO 2013/004265 A1 | 1/2013 |

(Continued)

OTHER PUBLICATIONS

International Search Report and Written Opinion of the International Searching Authority, dated Nov. 9, 2018, from International Application No. PCT/EP2018/025251, filed on Sep. 26, 2018. 10 pages.

(Continued)

*Primary Examiner* — Taylor V Oh
(74) *Attorney, Agent, or Firm* — HoustonHogle LLP

(57) ABSTRACT

The present invention relates to a process for preparing two mixtures of epoxidized fatty acid esters, comprising in the order given a transesterification of an epoxidized vegetable oil, followed by a reduction of the volatile saturated non-epoxidized fraction by short path distillation of the transesterified epoxidized vegetable oil, followed by a selection on the one hand of the non-vaporized fraction (residue) of the previous process step as the first mixture of epoxidized fatty acid esters and a selection on the other hand of the vaporized fraction (distillate) as the second mixture of epoxidized fatty acid esters. The first mixture is in particular suitable as plasticizer in halogenated polymers, the second mixture being particularly suitable as plasticizer in non-halogenated polymers.

17 Claims, 1 Drawing Sheet

(58) Field of Classification Search
USPC .......................................................... 549/561
See application file for complete search history.

(56) References Cited

FOREIGN PATENT DOCUMENTS

WO    WO 2013/055961 A1    4/2013
WO    WO 2014/135366 A1    9/2014

OTHER PUBLICATIONS

International Preliminary Report on Patentability, dated Mar. 31, 2020, from International Application No. PCT/EP2018/025251, filed on Sep. 26, 2018. 8 pages.

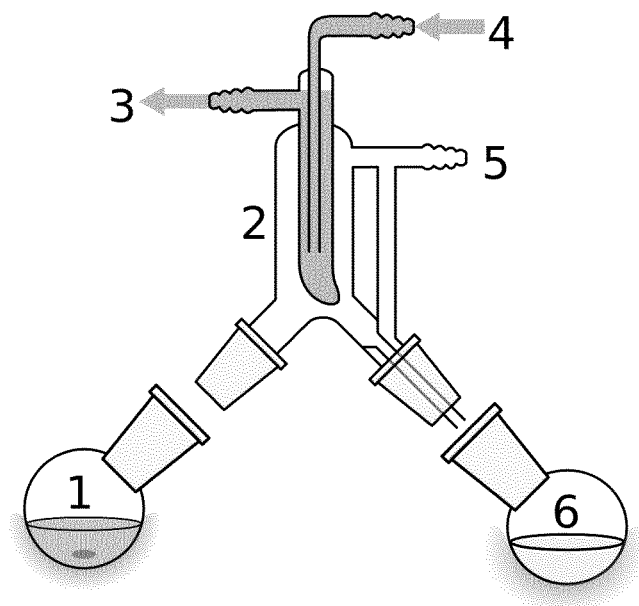

PROCESS FOR PREPARING MIXTURES OF EPOXIDIZED FATTY ACID ESTERS

RELATED APPLICATIONS

This application is a § 371 National Phase Application of International Application No. P07/EP2018/025251, filed on Sep. 26, 2018, now International Publication No. WO 2019/063130 A1, published on Apr. 4, 2019, which International Application claims priority to Belgian Application No. 2017/0138, filed on Sep. 27, 2017, both of which are incorporated herein by reference in their entirety.

FIELD OF THE INVENTION

The present invention relates to a new composition that can be used as plasticizer in polymer resins, in particular, polymer resins based on or containing polyvinylchloride. The invention also relates to a novel process for preparing such composition.

More in particular, the invention refers to a plasticizer comprising a distilled or purified epoxidized vegetable oil.

Such a plasticizer has quite specific properties with respect to the compatibility with the polymer resin. Further such a plasticizer is of at least partially bio-based or renewable origin. In this way, this invention helps to enhance the ecological durability of the final application.

BACKGROUND OF THE INVENTION

Plasticisers are used in various polymers to enhance their flexibility, and thereby transforming rigid material into flexible ones. By virtue hereof the possibilities and applications of these polymers are substantially enhanced. Plasticisers are used in various polymers, among which the most important are: polyvinylchloride, polyamide, polar rubbers and polyurethane.

Plasticisers are commonly incorporated into polyvinylchloride (PVC). PVC is a technically and economically very important polymer and is compounded in soft and rigid formulations for a large number of applications. Soft PVC compounds are obtained through combination of plasticisers and PVC resins. Important applications include amongst others cable jacketing, flooring materials, various coating applications and shoe soles.

Plasticisers usually are liquids that can be used in various technical processes. The physical characteristics of the plasticizers determine their scope of utilization. In particular the solubility parameters of a plasticiser have to match with the solubility parameters of the polymer to provide efficiency and lowest exudation.

Plasticisers for PVC are usually phthalic anhydride esters (phthalates). Still today about 80% of the worldwide plasticisers' consumption for PVC are related to phthalate compounds. They provide enhanced flexibility for a large number of applications. During PVC gelation, the plasticiser molecules solvate amorphous parts of the PVC macromolecules. "Gelation" is a usual term to describe the physical phenomenon occurring when polymer macromolecules entangle and form a continuous material. Since they are positioned in-between polymer chains and since they hold fatty chains, they avoid intermolecular bonding between PVC macromolecules and enhance the mobility of the PVC polymeric chains. Subsequently, PVC glass transition temperature is lowered. Plasticisers have the ability to couple substantially improved process properties to a high flexibility of the end product. The working principle of the above plasticisers relate to the so-called external plasticisers.

These are products that additionally are added to polymers during their formulation and/or their transformation; the plasticising effect is the result of a physical interaction with the polymer molecules, as described above.

There also exist internal plasticisers. These are polymeric material blended with PVC during compounding and by virtue hereof provide mechanical flexibility to the end-product. The present invention only relates to so-called external plasticisers.

Esters are the most interesting class of plasticisers. Apart from the earlier mentioned phthalate esters, also amongst others the following plasticisers are often found in actual applications: adipates, sebacates, maleates, gluterates, trimellitates, citrates, benzoates, sulfonamides, phosphate-esters, glycoletheresters, terephthalates, cyclohexane-dicarboxylates and polymeric plasticisers. Recently more plasticisers are being developed and used, partly or entirely synthesized from renewable and/or biobased raw materials. Examples of the latter are: citrate esters, epoxidized oils or fatty acid esters, acetylated monoglycerides.

PVC resins can be softened with plasticizers through all kind of usual polymeric material transformation processes: extrusion, calendering, injection moulding . . . . A particular field of applications is this whereby the PVC is suspended in the plasticiser and a plastisol is formed that can be coated on a substrate. Heating the coated substrate above the PVC glass transition temperature enables the plastisol to gel and form a thermoplastic film. The higher the temperature, the faster the gelation.

In coating processes, heating is the unique source of energy. That's why in most of the PVC coating applications, "general purpose" plasticisers are combined with specific plasticizers characterized by low molecular weight and excellent compatibility with PVC. Such co-plasticizers are called "fast fusers". They lower the required gelation energy and subsequently the time and/or temperature of PVC resins gelation. Traditional examples of these products are BBP (benzyl-butyl-phthalate) or ethyleneglycol-propyleneglycol di-benzoate. For this application, plasticizer compatibility with PVC impact even more final material performances than in calendering or extrusion process. This difference is due to absence of mechanical shearing forces.

Nowadays, petroleum-based plasticizers and polymer resins are widely used. These products, however, have various disadvantages, in particular, the accumulation of non-biodegradable plastics in the environment and the use of non-renewable resources. For this reason, during recent years, there is a growing interest in so-called bio-based materials as alternative solution for the traditional petroleum-based plasticizers and polymer resins. Bio-based materials are compounds obtained from molecules of vegetable origin.

Extensive research already has been performed in view of the development of such bio-based plasticizers.

Reference is made e.g. to the international patent application published as WO2013/055961 on Apr. 18, 2013, by Galata Chemicals LLC.

In said application, epoxidized vegetable oils, such as epoxidized soybean oil (ESBO) and epoxidized linseed oil (ELSO) have been disclosed as secondary plasticizers. However, both ESBO and ELSO are said to have limited compatibility with PVC due to their high molecular weight, while epoxidized mono-esters are known for their unacceptably high extraction out of the PVC matrix.

Several patents and patent applications are cited in said application, which relate to bio-based plasticizers derived from fatty acids containing epoxy functional groups. More specifically, said application is directed to a plasticizer composition for reduced plasticizer extraction from plasticized halogenated polymers comprising:

- an epoxidized fatty acid mono-ester comprising fatty acids derived from natural oils or animal fats and fully esterified with a monohydric alcohol and
- an epoxy-ester selected from amongst others epoxidized natural oils.

In view of the limited compatibility of e.g. ESBO with PVC, it is known to use ESBO as a stabilizer in PVC polymer resins, along with e.g. a benzoate or a citrate-based plasticizer. Such use has been disclosed e.g. in the published international patent application WO 2013/004265, published Jan. 10, 2013, by Tarkett GDL, Luxemburg. In this application a multilayer floor covering has been described, comprising in one of its layers a citrate-based plasticizer such as acetyl tributyl citrated (ATBC).

However, the use of bio-based compounds such as ESBO in larger amounts as primary or secondary plasticizer in halogenated polymers remains a problem, given its exudation tendency, caused by its quite limited compatibility with this kind of resins. This is in particular a problem in coating processes where no shearing forces are applied to the plastisol and where PVC gelation is only initiated thanks to oven heating.

In patent US 2002/0013396, in paragraphs [007] and [008], it is reminded that epoxidized soybean oil provides limited compatibility with PVC and cannot be incorporated at usual primary plasticizer dosage. Here is also underlined that ESBO (or ESO) based plasticizer incorporation as primary plasticizer requires a modification to let the solubility parameters match with PVC's ones.

In the patent application published as US 2016/0060426 A1, on Mar. 3, 2016, by Evonik Degussa GmbH, a process is described for preparing mixtures of epoxidized fatty acid esters. The various processes disclosed in said publication comprise:

- reducing the proportion of the fatty acids or fatty acid esters which do not have functional groups including multiple bonds in the fatty acid chain prior to (par 0064) or after (par 0066) the epoxidation of the fatty acids/fatty acid esters,
- an esterification in the case of epoxidized fatty acid esters and
- a transesterification in the case of epoxidized fatty acid esters.

So, in both cases (use of acids and use of esters), the reducing process step precedes the (trans-)esterification process step. The content of this publication will be addressed further in the present specification under the heading 'Detailed description of the invention'.

In spite of the various efforts and research as illustrated by the above prior art, there remains a continuing need for bio-based compounds such as ESBO to be used as plasticizer in halogenated resins such as PVC and its co-polymers, and to overcome their inherent low compatibility with the halogenated polymer resin matrix to be plasticized.

PROBLEM AND AIM OF THE INVENTION

The aim and object of the present invention is to solve the problems and overcome the above-mentioned drawbacks.

More in particular, the aim of the invention is to provide a process for the production of bio-based compounds or compositions that can be used as plasticizer in halogenated polymers, whereby the problem of exudation of the plasticizer out of the resin matrix does not occur.

As mentioned above, although the use of plasticizers in polymers may substantially enhance the flexibility, most of the plasticisers and in particular ESBO are characterized by an exudation phenomenon to the surface of the plasticized polymer. This, in turn, results in a slowly increasing brittleness.

So a more specific aim of the inventors is the development of a process for the production of bio-based plasticiser with an increased compatibility and a low exudation.

These objects and advantages are given only by way of illustrative example, and such objects may be exemplary of one or more embodiments of the invention. Other desirable objectives and advantages inherently achieved by the disclosed invention may occur or become apparent to those skilled in the art.

SUMMARY OF THE INVENTION

The invention is set forth and characterized in the main claim, while the dependent claims describe other characteristics and specific features for preferred embodiments of the invention.

According to one aspect of the invention, there are provided on the one hand a process for the production of bio-based compounds that can be used as plasticizer in halogenated polymers, said bio-based compounds comprising or consisting of epoxidized mono-esters and that are essentially free of volatile esters and on the other hand bio-based compounds that can be used as plasticizers in non-halogenated polymers.

According to a further aspect of the invention, there are provided such epoxidized mono-esters, that are essentially free of non-functionalized fatty acid-esters.

According to another aspect of the invention there is provided a process for preparing two mixtures of epoxidized fatty acid (mono-)esters, comprising in the order given:
1) epoxidation of a vegetable oil, followed by
2) transesterification of the epoxidized vegetable oil, followed by
3) short path distillation of the transesterified epoxidized vegetable oil, followed by
4) selection of the non-vaporized fraction of process step 3) as the first mixture of epoxidized fatty acid esters and
5) selection of the vaporized fraction of process step 3) as the second mixture of epoxidized fatty acid esters.

The main advantage of the short path distillation step is the reduction of the amount and/or the proportion of non-functionalized or non-epoxidized fatty acid esters in the residue or non-vaporized fraction resulting from this process step.

The inherent advantage hereof is that this fraction, hereinafter referred to as the first mixture, is particularly suitable as plasticizer in halogenated polymers.

According to a further aspect of the invention, the process is characterized in that the epoxidized vegetable oil is transesterified by 2-ethylhexanol, isoamyl alcohol or isononyl alcohol.

Further, the process yields two mixtures of epoxidized fatty acid esters prepared according to the process as set forth above, hereinafter referred to as the first, resp. the second mixture of epoxidized fatty acid esters.

According to a preferred mode of the process of the invention, the first mixture is characterized in that the weight amount of non-functionalized esters is less than 5%.

Further the mixtures of epoxidized fatty acid esters as obtained by the process as set forth above or as set forth in any of the process claims as set forth hereinafter can be used as plasticizers.

Further aspects and advantages of embodiments of the present invention will appear from the following description taken together with the accompanying drawing.

DETAILED DESCRIPTION OF EMBODIMENTS OF THE INVENTION

The following is a detailed description of the preferred embodiments of the invention.

The present application uses the term "short-path distillation" as it is conventionally used and understood by those practiced in the art of distilling chemical compositions. Within the framework of the invention, the term "short-path distillation" specifically is directed to single stage short-path distillation, as will be described hereinafter.

Short-path distillation is a distillation technique that involves the distillate travelling over a short distance, and is usually performed at reduced pressure.

The advantage of the reduced pressure is that the heating temperature can be held at a considerably lower level than the boiling point of the liquid to be processed at standard, e.g. atmospheric pressure. Further, the distillate in the apparatus wherein the short path distillation is performed, only has to travel over a short distance before condensing.

An example of a kind of apparatus that can be used for performing the short path distillation is a "Kugelrohr", comprising e.g. two glass chambers, separated by a vertical condenser fraction.

An example of such apparatus is shown in FIG. 1.

In said FIGURE, the following reference signs are used:
1 denotes the still pot with stirrer, comprising the composition to be distilled, hereinafter called the evaporator pot or bulb;
2 denotes the cold finger, bent to direct the distillate;
3 denotes the cooling liquid outlet;
4 denotes the cooling liquid inlet;
5 denotes the vacuum connection;
6 denotes the container for storing the distillate, hereinafter called the distillate pot or bulb.

As a cooling liquid, water can be used.

The short path distillation technique splits the starting product in two fractions, a distilled or vaporized fraction, hereinafter referred to as the distillate, and a non-vaporized fraction, comprising the heavier compounds that have not been distilled over to the distillate.

This non-vaporized or distilled fraction is hereinafter often referred to as "residue". The reduction of non-functionalized or non-epoxidized compounds in the mixture to be prepared according to the present invention is effected by selecting such non-vaporized fraction or "residue" as the final or desired product.

The distillate fraction is to be regarded as by-product of the process according to the invention that can be used as plasticiser for non-halogenated polymers.

Prior to performing the short-path distillation step according to the process of the present invention, the starting product may be de-gassed and/or its water content reduced.

Short path distillation apparatus suitable for performing the process according to the present invention are e.g. the Short Path Distillators available from UIC GmbH, a member of the BDI Group (BioEnergy International AG), Am Neuen Berg 4, 63755 Alzenau-Hörstein, Germany.

Standard Glass Short Path Distillators are marketed by said company under the trade names KDL 1, KDL 5, KDL 10 and KDL 30. Any of these laboratory plants are suitable for performing the short path distillation process according to the present invention provided the operating parameters of the process are optimized so as to achieve the objects of the present invention. As to operating parameters for the short path distillation, amount of vacuum, evaporator temperature and feed rate are key characteristics.

The lower the vacuum, the lower the temperature in the evaporator can be held, still to have an efficient distillation process. At atmospheric pressure, the boiling point of the soyate liquid compositions exceeds 300° C. Keeping the compositions at that temperature would quickly lead to an irreversible degradation of the mixture.

So, distillation under appropriate vacuum conditions is a prerequisite so as to attain the objects of the present invention.

The feed rate should be chosen such that the short path distillation apparatus is able to process the volume of liquid in the evaporator pot in an efficient manner, this means avoiding a too high residence time of the liquid in the evaporator pot.

The temperature in the condenser can be chosen within broad limits, as long as it allows an efficient condensation of the distillate.

In the short path distillation process according to the present invention, the pressure preferably is kept below 0.5 mbara, preferably below 0.1 mbara. (mbara stands for millibar absolute)

Further, In the short path distillation process according to the present invention, the temperature in the evaporator pot of the short path distillation process and apparatus should be kept in the range of 120-200° C., preferably in the range of 120-180° C., most preferably in the range of 120-160° C.

The temperature in the condenser is less critical; it suffices to keep same within a range whereby the distillate condenses.

For the composition to be distilled according to the present invention, the condenser temperature may be kept e.g. within the range of 20-55° C., preferably within 30-45° C., e.g. around 35° C.

The feed rate of the composition to be distilled may vary between broad ranges, and should conform to the overall size of the short path distillation apparatus used.

Two types of short path distillation are available: single and dual stage distillation.

In a single stage distillation, the product is only once short path distilled.

In a dual stage distillation, the product of interest is twice short path distilled e.g. in the first stage the 'lower' boiling products are removed and the residue is subjected to a second stage where the product of interest ends up in the distillate. So, in the second stage the product of interest is freed from the 'higher' boiling products.

In the process according to the present invention, preferably single stage short path distillation is applied.

The term isoamyl alcohol as used in the present specification and the claims, refers to either 3-methylbutanol, or while bio-based isoamylalcohol is used, refers to a mixture of 3-methylbutanol and 2-methylbutanol, the latter compounds being present according to a preferred embodiment of the present invention in a ratio of approximately 80/20% by weight.

In the present specification and the claims, all percentages (%) are by weight, unless indicated otherwise.

The process according to the present invention differs substantially and is also not obvious from the process and the teaching disclosed in the patent application published as US 2016/0060426 A1, on Mar. 3, 2016, by Evonik Degussa GmbH. The process described in the general description of said patent application comprises the following steps in the sequence indicated below (reference being made to e.g. paragraph (0130 a.f.) of this application as published:
a) obtaining a fatty acid ester mixture, preferably from a vegetable oil;
b) epoxidizing the mixture;
c) reducing the proportion of the non-epoxidized fatty acid esters in the mixture by means of distillation;
d) optionally transesterifying the mixture from step c).

So, according to this publication, the transesterification takes place after the distillation, whereas in the process according to the present invention, the opposite sequence of process steps is applied: distillation after transesterification.

Further, according to this disclosure, the epoxidation is performed on the fatty acid ester mixture, or alternatively on the fatty acids, whereas in the process according to the invention, the epoxidation step is performed on the vegetable oil.

Various alternative process steps are set forth in this patent application, e.g. whereby in case in step a) fatty acids are used, in step d) an esterification takes place.

As a further alternative process, according to paragraph (0152), a mixture is prepared comprising the following steps, in the order given:
a) obtaining a fatty acid mixture or a fatty acid ester mixture;
b) reducing the proportion of the saturated fatty acids or the saturated fatty acid esters, preferably by means of crystallisation;
c) epoxidizing the mixture from step b);
d) esterifying or optionally transesterifying the mixture from step c).

Also, in this process, e.g. according to paragraph (0157) the transesterification can take place between steps b) and c). However, also in this case, contrary to the present invention, the transesterification takes place after the distillation.

A similar process sequence is described in said application, reference being made to paragraphs (0086) up to (0096).

So, the general teaching of this disclosure amounts to a process comprising the following steps in the given sequence:
1) preparing a methyl ester of a natural oil;
2) epoxidation of the methyl ester mixture;
3) depletion, being a reduction of the remaining saturated esters by distillation or crystallisation;
4) transesterification of the mono-esters.

The process of the present invention differs from the processes described in said patent publication by at least two characteristics:
the epoxidation is performed on the natural oil, not on the ester mixture;
process step 1) is not applied, process step 4) is applied as a second step and process step 3 is the final process step. As will be clarified hereinafter, the process step 3 according to the present invention is applied in a quite differently manner. Differently phrased, in the sequence of processes according to the present invention, the distillation and in particular the selection of the residue on the one hand and the distillate on the other hand is the final step of the entire process sequence. Example 14 of this application, contrary to the general teaching of the application, discloses a process wherein transesterification precedes distillation.

Reference is being made to paragraph (0244) describing the transesterification, and paragraph (0248) describing the distillation process step. However, Table 15 sets forth the results of such distillation step, and the last two lines indicate that the residue makes up only 12, resp. 17% by mass, whereas the distillate makes up 88, resp. 83% by mass.

This is completely contrary to the process described in the present invention, since in the process of the present invention, the non-vaporized or residue fraction is selected as the final product for the first mixture, preferably comprising a weight amount of non-functionalized esters less than 5%.

Neither the inverted sequence of process steps, neither the fact that the non-vaporized or residue fraction is selected as one of the final products in the sequence of process steps of the present invention is disclosed or rendered obvious in this application. Further, this application does not contain any hint or guidance that would guide or direct the person skilled in the art to the present invention; rather it hints to the opposite way, namely applying the distillation process step before the transesterification step and/or selecting the distillate rather than the residue of the distillation step as the final product.

Further, the process of the present invention also differs from and is not obvious from the process described in the international patent publication of Evonik Industries AG, Germany, published as WO 2014/135366A1 on Sep. 12, 2014.

According to e.g. claims 5 and 6 of this application, the epoxidation step is also performed on the fatty acid mixture (claim 5) or on the fatty ester mixture (claim 6). According to page 2, line 26 and page 3 line 1, the process steps b), c) and d) can be performed in any given order. As regards step a) such a statement has not been made, implying that according to the teaching of this document, this process step necessarily should be performed as a first step. This step a) relates to the production of a fatty acid mixture, or a fatty ester mixture from the vegetable oil.

Hereupon the various other process steps are applied, including the epoxidation step. This again is quite different from the process of the present invention, wherein the epoxidation is performed directly on the natural vegetable oil.

Regarding the transesterification step comprised in the sequence of process steps of the present invention:

According to the transesterification reaction scheme set forth hereinafter, ESBO (Epoxidized Soy Bean Oil) is transesterified by 2-ethylhexanol to glycerol on the one hand and a functionalized fatty acid ester on the other hand (epoxidized 2-ethylhexyl soyate, as explained hereinafter).

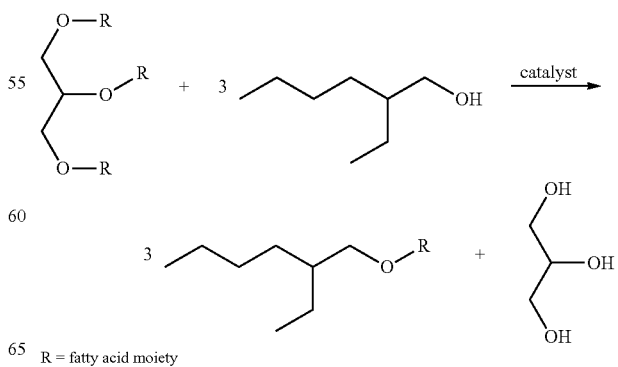

R = fatty acid moiety

Alternatively, In the transesterification reaction scheme set forth hereinafter, ESBO is transesterified by isoamyl alcohol to glycerol on the one hand and a functionalized fatty acid ester on the other hand (epoxidized isoamyl soyate, as explained hereinafter).

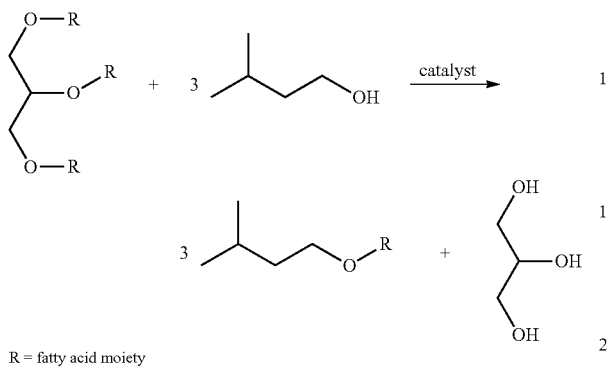

R = fatty acid moiety

In both of the above transesterification reaction schemes, contrary to the presently known transesterification processes using a sodium methylate as catalyst, the alkali alkoxide of the corresponding alcohol is used as transesterification catalyst, more in particular potassium or sodium alkoxide.

Such a product, the alkali isoamyl alcoholate, more in particular potassium or sodium isoamyl alcoholate, has e.g. been described in the US patent application published under the number US 2012/0289727 A1 in the name of NPC Industrias Quimicas AS LTDA.

A suitable production mode for such catalyst is described hereinafter.

In principle, three reaction or synthesis routes are possible for the alkoxide catalyst:

1) Reaction of an alcohol, in particular isoamyl alcohol or 2-ethylhexanol, with the alkali metal such as (metallic) sodium, followed by removal of the hydrogen;
2) Reaction of an alcohol, in particular isoamyl alcohol or 2-ethylhexanol, with an alkali hydroxide such as sodium hydroxide, followed by removal of water;
3) Exchange reaction (transalkoxylation) of an alcohol, in particular isoamyl alcohol or 2-ethylhexanol, with another alkoxide, followed by removal of the alcohol originating from the starting alkoxide.

In case the third synthesis route is used, as a starting material, an alkali methoxide such as sodium methoxide (also called sodium methylate) can be used given its industrial availability. It can be used either in powder form or as a solution in methanol. The solution is the preferred mode, given the difficulty in handling the powder form.

The transesterification scheme by means of the catalyst is shown hereinafter:

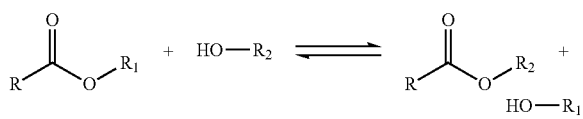

The reaction with a sodium alkoxide as catalyst comprises two consecutive steps.

Step 1:

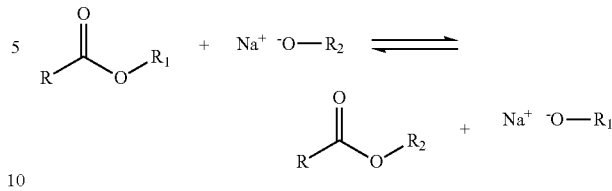

In the second step, the alkoxide catalyst is regenerated by reaction with the excess of alcohol HO—$R_2$, this being also an equilibrium reaction.

Step 2:

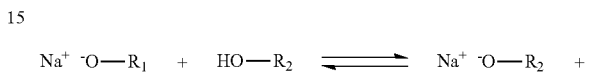

EXAMPLES

In the following, the present invention will be described in more detail with reference to specific examples thereof.
Series of Examples Relating to Epoxidized Isoamylsoyate:
General:
Production of Epoxidized Isoamyl Soyate:

533.1 g of predried (120° C., 12 mbara) ESBO is added to 289.1 g solution of isoamyl alcohol containing 5.93 wt % of sodium isoamyl alcoholate at 58° C. in a mechanically stirred, jacketed 1 L glass reactor. After 30 min of reaction, the stirring was stopped and 43.3 g of glycerol phase was removed. 180 g of demineralized $H_2O$ was added, followed by of 85% $H_3PO4$ in $H_2O$ to pH 7.3. The water phase was decanted and removed. The organic phase was washed with an additional 180 g of demineralized $H_2O$. The excess of isoamyl alcohol was removed by heating up to 125° C. and 19 mbara. After cooling to 50° C., 10.2 g of 29 wt % NaOH in $H_2O$ and 9.5 g 30 wt % $H_2O_2$ in $H_2O$ is added. After 15 min 153.1 g of demineralized $H_2O$ is added, decanted and removed. The organic phase is washed with an additional 149.8 g demineralized $H_2O$, followed by drying up to 125° C. in vacuo. After cooling to room temperature, the product is filtered with a Seitz T750 filter plate and 564.8 g of product is obtained.

Short Path Distillation of Epoxidized Isoamyl Soyate:

A short path distillation process step was applied on behalf of applicant by a third party, Ecosynth N.V., Industrielaan 12, B-9800 Deinze, Belgium, to epoxidized isoamyl soyate in a small scale KDL 1 apparatus of UIC GmbH, as mentioned supra.

The overall set-up was as follows: the sample was washed and dried in a 5 L jacketed glass reactor with mechanical stirrer, dip tube for air, thermocouple, dean-stark with water cooled vertical condenser and membrane pump for the vacuum.

The short path distillation unit of Ecosynth was used and operated by Ecosynth on behalf of applicant. The setup is a KDL1 ex UIC with possibility to heat up the evaporator and condenser with different thermostats. The following ranges of process characteristics were used:
vacuum: 0.006-0.03 mbara;
evaporator temperature: up to 135° C.;
feed rate: 2.4-3.0 ml/min.

Two series of tests were run, a first series of 4 tests, followed by a second series of 7 tests.
First Series of Tests:

More in particular, a first series of four tests has been performed, the results whereof are set forth in the following table. Tests 1/1, 1/2 and 1/3 represent less favorable test results, whereas test 1/4 represents a test according to a preferred mode of the invention:

|  | Test 1/1 | Test 1/2 | Test 1/3 | Test 1/4 |
|---|---|---|---|---|
| Pressure (mbara) | 0.025 | 0.018-0.021 | 0.016 | 0.021-0.024 |
| Evap. temp (° C.) | 120 | 125 | 130 | 135 |
| Feed rate (ml/min) | 4.74 | 3.88 | 3.20 | 3.02 |
| Residue (wt %) | 93.5 | 86.2 | 76.3 | 71.5 |
| Distillate (wt %) | 6.5 | 13.8 | 23.7 | 28.5 |

'Evap. temp' denotes the temperature in the evaporator bulb.

The temperature in the condenser amounted to 40° C. for all tests.

The wiper speed in the evaporator bulb amounted to 350 rpm for all tests.

The residue and distillate amounts are expressed in weight %; together they amount to 100%.

Second Series of Tests:

In a second series of tests, the above test 1/4, being the test according to a preferred mode of the invention, has been repeated seven times, with the following process characteristics:

vacuum: 0.006-0.032 mbara;
evaporator temperature: 135° C.;
feed rate: 2.46-3.03 ml/min.

The process characteristics and results of this second series of tests is set forth in the below table:

|  | Test 2/1 | Test 2/2 | Test 2/3 | Test 2/4 | Test 2/5 | Test 2/6 | Test 2/7 |
|---|---|---|---|---|---|---|---|
| Pressure (mbara) | 0.014-0.018 | 0.014-0.025 | 0.014-0.020 | 0.012-0.021 | 0.013-0.032 | 0.009-0.016 | 0.006-0.021 |
| Feed rate (ml/min) | 2.48 | 2.81 | 3.03 | 2.79 | 2.41 | 2.46 | 2.66 |
| Residue (wt %) | 65.78 | 66.64 | 69.90 | 65.96 | 63.61 | 64.92 | 65.59 |
| Distillate (wt %) | 34.22 | 33.36 | 30.10 | 34.04 | 36.39 | 35.08 | 34.41 |
| Mass residue (g) | 212.77 | 144.38 | 177.08 | 76.97 | 138.03 | 137.93 | 194.98 |
| Mass distillate (g) | 110.70 | 72.27 | 76.27 | 39.73 | 78.98 | 74.53 | 102.27 |

The wiper speed in the evaporator bulb amounted to 350 rpm for all batches.

The temperature in the condenser amounted to 40° C. for all tests.

The table set forth below shows the analysis results of the fractions, namely the distillate on the one hand and the residue on the other hand, of the first series of tests. In this table, Dis 1/X refers to the Distillate X resulting from the above Test X (1 up to 4). Likewise, Res 1/X refers to the Residue X resulting from the above Test X (1 up to 4).

The table set forth below shows the aggregate analysis results of the fractions, namely the distillate on the one hand and the residue on the other hand, of the second series of tests. By aggregate is meant that the fractions, namely distillate and residue respectively, of the second series of tests have been added, and that the analysis has been performed on the added distillate, resp. residue fractions.

|  | Start | Dist | Res |
|---|---|---|---|
| Color (APHA) | 51 | 2 | 91 |
| Oxirane (%) | 5.47 | 3.88 | 6.26 |
| C16 | 11.24 | 30.07 | 0.56 |
| C18 | 4.17 | 8.94 | 1.25 |
| C18:1 | 21.26 | 27.71 | 17.32 |
| C20 | 0.55 | 0.57 | 0.48 |
| C18:2 | 43.56 | 26.07 | 51.95 |
| C18:3 | 6.52 | 1.31 | 9.88 |
| C22 | 1.00 | 0.29 | 1.65 |
| ESBO |  |  | 2.38 |
| % non-functionalized | 16.96 | 39.87 | 3.94 |

The amounts of the fractions C 16 up to C18:3 have been determined by liquid gas chromatography.

C:16 up to C18:3 refers to the various fractions of the mixture of esters comprising from 16 up to 18 carbon atoms in the fatty acid chain.

':1' denotes the chains being mono-epoxidized, ':2' denotes the chains being di-epoxidized, ':3' denotes the chains being tri-epoxidized.

If none of the marks:1, :2 or :3 appears, it indicates that the respective fatty acid chain does not carry any epoxy group, so it represents a non-functionalized fatty acid ester. Fatty acid esters carrying an amount of carbon atoms equal to or lower than 15, are practically not present in the epoxidized fatty acid ester starting product; likewise, fatty acid esters carrying an amount of carbon atoms equal to or above 22, are practically not present in the epoxidized fatty acid ester starting product.

The last row indicates the sum of such non-functionalized fatty acid esters in the distillate, respectively in the residue obtained by the short path distillation step; this is the sum of

|  | Start | Dis 1/1 | Res 1/1 | Dis 1/2 | Res 1/2 | Dis 1/3 | Res 1/3 | Dis 1/4 | Res 1/4 |
|---|---|---|---|---|---|---|---|---|---|
| Oxirane (%) | 5.47 | 2.16 | 5.68 | 2.60 | 5.87 | 2.71 | 6.19 | 3.58 | 6.25 |
| C16 | 11.24 | 56.10 | 7.24 | 48.33 | 4.30 | 37.53 | 1.73 | 33.59 | 0.98 |
| C18 | 4.17 | 8.27 | 3.78 | 9.04 | 3.18 | 9.62 | 2.23 | 9.39 | 1.70 |
| C18:1 | 21.26 | 15.81 | 21.57 | 18.67 | 21.40 | 23.37 | 19.38 | 25.89 | 18.80 |
| C20 | 0.55 | 0.34 | 0.59 | 0.39 | 0.59 | 0.55 | 0.56 | 0.58 | 0.52 |
| C18:2 | 43.56 | 12.06 | 45.44 | 16.29 | 46.72 | 21.11 | 49.47 | 23.35 | 50.15 |
| C18:3 | 6.52 | 0.65 | 8.60 | 1.10 | 9.28 | 1.59 | 10.29 | 1.67 | 10.82 |
| C22 | 1.00 | 0.12 | 1.28 | 0.17 | 1.35 | 0.29 | 1.50 | 0.32 | 1.54 |
| ESBO |  |  |  |  | 1.39 |  | 1.59 |  | 1.94 |
| % non-functionalized | 16.96 | 64.83 | 12.89 | 57.93 | 9.42 | 47.99 | 6.02 | 43.88 | 4.74 | the fatty acid esters comprising C16, C18, C20 and C22 compounds, and not bearing any functional epoxy group.

The oxirane number is a measure for the number of epoxide functional groups in the product concerned and is defined as a percentage % of oxygen atoms stemming from epoxy groups in the product. So it is directly representative of the amount of exoxy groups in the fatty acid chain.

The oxirane number has been determined using the following procedure:

By means of a manual titration with 0.1 M $HClO_4$ in acetic acid, ±0.5 g of sample product is weighed in an Erlenmeyer (note to 1 mg) and dissolved in 10 ml of ethyl acetate and 10 ml of tetraethylammonium bromide solution in acetic acid (50 g $Et_4NBr$+250 ml acetic acid). One drop of cristal violet (1% in acetic acid) is added as pH indicator. The colour changes from purple to green when all epoxides in the sample have reacted.

Conclusions

With respect to the residue fraction of the short path distillation process, the short path distillation process step has lowered significantly the amount of non-functionalized fatty acid esters.

All mono-esters are evaporated to some extent, but the C20 is the transition point. This means that products with a retention time on the gas-chromatograph shorter than C20 are enriched with acid esters in the distillate, whereas products with a retention time on the gas-chromatograph larger than C20 are enriched in the residue. C20 relates to the number of carbon atoms of the fatty acid. The number of carbon atoms of the ester is higher, namely +5 for isoamyl, +8 for 2-ethylhexyl.

The proportion of more volatile compounds in the residue is less compared to the starting mixture, while the proportion of less volatile compounds in the residue is larger compared to the starting mixture, before the implementation of the short path distillation process step.

A complete transfer by distillation of the non-functionalized mono-esters from the starting mixture to the distillate is not economical due to the high loss on raw material. Hence, the residue still contains 3.9% of non-functionalized mono-esters.

The distillate is almost colorless, while the residue is more colored. Most of the increase in color is due to the concentration effect.

Series of Examples Relating to Epoxidized 2-ethyl hexylsoyate:
General:
Production of Epoxidized 2-Ethyl Hexylsoyate:

521.5 g of predried (120° C., 12 mbara) ESBO is added to 426.5 g solution of 2-ethylhexanol containing 5.17 wt % sodium 2-ethylhexanolate at 62° C. in a mechanically stirred, jacketed 1 L glass reactor. The reaction mixture turned brown after 30 s. After 1h20 the stirring was stopped and 39.3 g of glycerol phase was removed. 124 g of demineralized $H_2O$ was added, followed by 1.5 ml of 85% $H_3PO4$ in $H_2O$ to neutralize the remaining catalyst. The water phase was decanted and removed. The organic phase was washed with an additional 120.8 g of demineralized $H_2O$. The excess of 2-ethylhexanol was removed by heating up to 125° C. and 8 mbara. After cooling to 40° C., 4.55 g of 29 wt % NaOH in $H_2O$ and 3.26 g 30 wt % $H_2O_2$ in $H_2O$ is added. After 15 min 150.6 g of demineralized $H_2O$ is added, decanted and removed. The organic phase is washed with an additional 150.5 g demineralized $H_2O$, followed by drying up to 120° C. in vacuo. After cooling to room temperature, the product is filtered with a Seitz T750 filter plate and 642.6 g of product is obtained.

Short Path Distillation of Epoxidized 2-Ethyl Hexylsoyate:

A short path distillation process step was applied to epoxidized 2-ethylhexyl soyate in a small scale KDL X apparatus of UIC GmbH, as mentioned supra, with the following process characteristics:
vacuum: 0.009-0.02 mbara;
evaporator temperature: 148° C.;
feed rate: 1.8-1.95 ml/min.

Goal of the various tests as performed was to obtain two mixtures of epoxidized 2-ethylhexyl soyate compounds, suitable as plasticizers, wherein the first mixture is characterised by low amounts of residual 2-ethylhexanol and non-functionalized fatty acid esters (the residue of the short path distillation process step). The distillate then representing the second mixture, in particular is suitable as plasticizer in non-halogenated polymers. A similar conclusion may be drawn for the example relating to the epoxidized isoamyl soyate.

Prior to the short-path distillation step, the 2-ethyl hexylester of epoxidized soybean oil after transesterification was purified to obtain a product with low acid index and water content. That purified product was thereafter subjected to a short-path distillation step.

The set-up was as follows: a 5 L jacketed glass reactor with mechanical stirrer, dip tube for air, thermocouple, dean-stark with water cooled vertical condenser and membrane pump for the vacuum.

The short path distillation unit of Ecosynth (as far the previous series of examples) was used and operated by Ecosynth on behalf of applicant. The setup is a KDL1 ex UIC with possibility to heat up the evaporator and condenser with different thermostats. Washing and drying of the 2-ethylhexyl ester: 4578 g of the 2-ethylhexyl ester (acid index 1.07 mg KOH/g) was washed at 60° C. with 1068 g of demineralized water and 16.6 g 25% NaOH. 1123 g water phase was removed after decantation.

1141 g of demineralized water was added at 60° C. and after decantation 1124 g water phase was removed. The product was dried under vacuum up to 115° C. (mass) and 30 mbara.

First Series of Tests:

In the table set forth below, tests 1/1, 1/2, 1/3 and 1/5 represent less favorable test results, whereas test 1/4 is according to a preferred mode of the invention.

|  | Test 1/1 | Test 1/2 | Test 1/3 | Test 1/4 | Test 1/5 |
|---|---|---|---|---|---|
| $T_{evap}$ (° C.) | 130 | 135 | 140 | 145 | 145 |
| $T_{cond}$ (° C.) | 40 | 40 | 40 | 40 | 40 |
| P (mbara) | 0.016-0.018 | 0.011-0.019 | 0.0093-0.019 | 0.012-0.017 | 0.0094-0.014 |
| Wiper blade speed (RPM) | 350 | 350 | 350 | 350 | 350 |
| Feed time (min) | 22.0 | 34.2 | 29.8 | 30.9 | 19.7 |
| Feed rate (ml/min) | 1.82 | 1.87 | 2.02 | 1.94 | 3.05 |
| Feed rate (g/min) | 1.66 | 1.71 | 1.84 | 1.77 | 2.78 |
| Mass distillate (g) | 4.30 | 10.38 | 11.56 | 15.41 | 11.72 |
| Mas residue (g) | 30.09 | 45.95 | 40.58 | 36.72 | 41.46 |
| M % distillate | 12.5 | 18.4 | 22.2 | 29.6 | 22.0 |
| M % residue | 87.5 | 81.6 | 77.8 | 70.4 | 78.0 |

$T_{evap}$ denotes the temperature in the evaporator bulb;
$T_{cond}$ denotes the temperature in the condenser bulb;
M % distillate denotes the mass percentage of the distillate;
M % residue denotes the mass percentage of the distillate.

Second Series of Tests:

The test according to the preferred mode of the invention as set forth above under test 1/4, has been repeated four times under the process conditions set forth below.

|  | Test 2/1 | Test 2/2 | Test 2/3 | Test 2/4 |
|---|---|---|---|---|
| $T_{evap}$ (° C.) | 148 | 148 | 148 | 148 |
| $T_{cond}$ (° C.) | 40 | 40 | 40 | 40 |
| P (mbara) | 0.0093-0.018 | 0.0093-0.017 | 0.0094-0.018 | 0.0089-0.019 |
| Wiper blade speed (RPM) | 350 | 350 | 350 | 350 |
| Feed time (min) | 364 | 426 | 413 | 408 |
| Feed rate (ml/min) | 1.87 | 1.95 | 1.80 | 1.91 |
| Feed rate (g/min) | 1.70 | 1.78 | 1.64 | 1.74 |
| Mass distillate (g) | 208.4 | 246.6 | 234.5 | 240.1 |
| Mas residue (g) | 410.7 | 510.7 | 443.5 | 469.0 |
| M % distillate | 33.7 | 32.6 | 34.6 | 33.9 |
| M % residue | 66.3 | 67.4 | 65.4 | 66.1 |

Abbreviations in the above left column have the same meaning as in the table set forth under the heading "First series of tests".

The results stemming from the gas-chromatographic analysis performed on each of the residues and distillates resulting from the first series of tests are set forth in the table below.

|  | Start | Res 1/1 | Dist 1/1 | Res 1/2 | Dist 1/2 | Res 1/3 | Dist 1/3 |
|---|---|---|---|---|---|---|---|
| Oxirane number (%) | 4.91 | 5.24 | 2.17 | 5.39 | 2.64 | 5.41 | 2.95 |
| C16 | 11.5 | 4.84 | 50.91 | 3.30 | 42.74 | 2.81 | 37.37 |
| C18 | 4.20 | 3.51 | 8.81 | 3.00 | 8.99 | 2.65 | 9.01 |
| C18:1 | 23.18 | 23.45 | 18.96 | 23.03 | 22.76 | 22.68 | 24.96 |
| C20 | 0.42 | 0.47 | 033 | 0.46 | 0.40 | 0.44 | 0.44 |
| C18:2 | 45.75 | 50.45 | 14.92 | 52.36 | 19.14 | 54.24 | 22.24 |
| C22 | 0.58 | 0.80 | 0.10 | 0.74 | 0.13 |  | 0.15 |
| C18:3 | 6.38 | 7.34 |  | 7.81 |  | 8.06 |  |
| Non-functionalized % | 16.7 | 9.6 | 60.2 | 7.5 | 52.3 | 5.9 | 47.0 |

|  | Start | Res 1/4 | Dist 1/4 | Res 1/5 | Dist 1/5 |
|---|---|---|---|---|---|
| Oxirane number (%) | 4.91 | 5.50 | 3.30 | 5.40 | 2.92 |
| C16 | 11.50 | 1.13 | 32.14 | 2.68 | 38.26 |
| C18 | 4.20 | 1.92 | 8.83 | 2.66 | 8.87 |
| C18:1 | 23.18 | 20.91 | 27.42 | 22.50 | 24.52 |
| C20 | 0.42 | 0.45 | 0.49 | 0.43 | 0.43 |
| C18:2 | 45.75 | 56.60 | 25.41 | 54.00 | 21.96 |
| C22 | 0.58 |  | 0.18 |  | 0.15 |
| C18:3 | 6.38 | 8.96 |  | 8.12 |  |
| Non-functionalized % | 16.7 | 3.5 | 41.6 | 5.8 | 47.7 |

The results stemming from the gas-chromatographic analysis performed on the second test are set forth in the table below.

|  | Start | Res | Dist |
|---|---|---|---|
| Oxirane number (%) | 4.91 | 5.64 | 3.55 |
| Water (%) | 0.021 | 0.018 | 0.016 |
| Color (APHA) | 48 | 64 | 8 |
| C16 | 11.50 | 0.87 | 28.90 |
| C18 | 4.20 | 1.62 | 8.52 |
| C18:1 | 23.18 | 19.79 | 28.51 |
| C20 | 0.42 | 0.46 | 0.51 |
| C18:2 | 45.75 | 57.01 | 27.80 |
| C22 | 0.58 | 0.87 | 0.18 |
| C18:3 | 6.38 | 8.79 |  |
| Non-functionalized % | 16.7 | 3.8 | 38.1 |

Conclusions

- the total % of di-epoxidized compounds (C18:2) in the residue (first mixture) amounts to 57.01%;
- the total % of tri-epoxidized compounds in the residue amounts to 8.79%;
- short path distillation lowers significantly the amount of non-functionalized fatty acid esters: from 16.7% in the starting material to 3.8% in the residue;
- almost all fatty acid esters are evaporated to some extent, but the C20 is the transition point, as described earlier;
- complete removal of the non-functionalized fatty acid esters is not economical due to the high loss on raw material; the residue still contains 3.8% (sum of C16, C18, C20 and C22) non-functionalized esters.
- the distillate is almost colorless, while the residue is more colored due to the concentration effect.

Given the substantial reduction of non-functionalized fatty acid esters in the residue (non-vaporized fraction) obtained by the short path distillation process step, this non-vaporized fraction or residue can be retained as the first mixture of epoxidized fatty acid esters according to the invention.

This first mixture is particularly suitable as plasticizer, in particular as plasticizer in halogenated polymers.

The vaporized fraction or distillate resulting from the short path distillation process step can be selected as the second mixture of epoxidized fatty acid esters, suitable as plasticizer, in particular in non-halogenated polymers.

According to a preferred embodiment of the process of the invention, the first mixture of epoxidized fatty acid esters is particularly suitable as plasticizer in halogenated polymers, provided:

the weight amount of non-epoxidized esters in such first mixture is less than 5%, the weight amount of di-epoxidized esters in the mixture is more than 48%, and the weight amount of tri-epoxidized esters in the mixture is less than 10%.

According to a further preferred embodiment, such first mixture as plasticizer further comprises a dialkylterephthalate or a dialkyl ester of cyclohexane-1,2-, -1,3- or -1,4-dicarboxylic acid. According to a still further preferred embodiment, such plasticizer further comprises dioctylterephthalate and/or di-isononyl-1,2-cyclohexanedicarboxylate.

Still further, in the plasticizer the ratio of the mixture of epoxidized fatty acid esters in the overall plasticizer composition is from 25 to 50% by weight.

Such plasticizer in particular is suitable for being used in one or more polymers selected from the group consisting of polyvinyl chloride, a copolymer of vinyl chloride with vinyl acetate or with butyl acrylate, polyalkyl methacrylate, polyvinyl butyral, polyurethane, polylactic acid, polyhydroxybutyral and nitrocellulose.

Further, such plasticizer can be used as fast fusers along with more traditional plasticizers such as DINCH or DOTP in halogenated polymers, e.g. PVC.

In the claims as set forth hereinafter, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A process for preparing two mixtures of epoxidized fatty acid esters, comprising in the order given:
   a) epoxidizing a vegetable oil to form an epoxidized vegetable oil, followed by
   b) transesterifying the epoxidized vegetable oil to form a transesterified epoxidized vegetable oil having epoxidized fatty acid esters, followed by
   c) distilling the transesterified epoxidized vegetable oil, followed by
   d) selecting a non-vaporized fraction of process step c) as a first mixture of epoxidized fatty acid esters; and
   e) selecting a vaporized fraction of process step c) as a second mixture of epoxidized fatty acid esters.

2. The process according to claim 1, wherein the vegetable oil includes soybean oil or linseed oil or both.

3. The process according to claim 1, wherein the epoxidized vegetable oil is transesterified by 2-ethylhexanol, isoamyl alcohol or isononyl alcohol.

4. The process according to claim 3, wherein at least three moles of alcohol for every one mole of epoxidized vegetable oil is used.

5. The process according to claim 3, wherein in case the epoxidized vegetable oil is transesterified by 2-ethylhexanol, an alkali 2-ethylhexanolate is used as a catalyst, in case the epoxidized vegetable oil is transesterified by isoamyl alcohol, an alkali isoamyl alcoholate is used as a catalyst, and in case the epoxidized vegetable oil is transesterified by isononyl alcohol, an alkali isononyl alcoholate is used as a catalyst.

6. The process according to claim 5, wherein the alkali 2-ethylhexanolate, comprises the catalyst sodium 2-ethylhexanolate or potassium 2-ethylhexanolate.

7. The process according to claim 5, wherein alkali isoamyl alcoholate comprises the catalyst sodium isoamyl alcoholate or potassium isoamyl alcoholate.

8. The process according to claim 5, wherein alkali isononyl alcoholate comprises the catalyst sodium isononyl alcoholate or potassium isononyl alcoholate.

9. The process according to claim 1, wherein the pressure during the short path distillation is below 0.5 mbara.

10. The process according to claim 1, wherein the pressure during the short path distillation is below 0.25 mbara.

11. The process according to claim 1, wherein the pressure during the short path distillation is below 0.1 mbara.

12. The process according to claim 1, wherein the evaporator temperature during the short path distillation is in the range of 120–200° C.

13. The process according to claim 1, wherein the evaporator temperature during the short path distillation is in the range of 120–180° C.

14. The process according to claim 1, wherein the evaporator temperature during the short path distillation is in the range of 120–160° C.

15. The process according to claim 1, wherein the epoxidized vegetable oil is transesterified by 2-ethylhexanol in the presence of an alkali 2-ethylhexanolate.

16. The process according to claim 1, wherein the epoxidized vegetable oil is transesterified by isoamyl alcohol in the presence of an alkali isoamyl alcoholate.

17. The process according to claim 1, wherein the epoxidized vegetable oil is transesterified by isononyl alcohol in the presence of an alkali isononyl alcoholate.

* * * * *